United States Patent
Ho et al.

(10) Patent No.: US 10,251,781 B2
(45) Date of Patent: Apr. 9, 2019

(54) RESTORATION OF ACCOMMODATION BY LENS REFILLING

(75) Inventors: Arthur Ho, Sydney (AU); Jean-Marie Parel, Miami, FL (US); Jukka Moilanen, Helsinki (FI); Paul Mendell Erickson, Mill Hall, PA (US)

(73) Assignee: Adventus Technologies, Inc., Irvine, CA (US)

( * ) Notice: Subject to any disclaimer, the term of this patent is extended or adjusted under 35 U.S.C. 154(b) by 524 days.

(21) Appl. No.: 14/006,082

(22) PCT Filed: Mar. 20, 2012

(86) PCT No.: PCT/AU2012/000290
§ 371 (c)(1),
(2), (4) Date: Sep. 18, 2013

(87) PCT Pub. No.: WO2012/126053
PCT Pub. Date: Sep. 27, 2012

(65) Prior Publication Data
US 2014/0012240 A1 Jan. 9, 2014

Related U.S. Application Data

(60) Provisional application No. 61/454,941, filed on Mar. 21, 2011.

(51) Int. Cl.
*A61F 2/16* (2006.01)
*A61F 9/008* (2006.01)
(Continued)

(52) U.S. Cl.
CPC ........ *A61F 9/00736* (2013.01); *A61F 9/0017* (2013.01); *A61F 9/00838* (2013.01);
(Continued)

(58) Field of Classification Search
None
See application file for complete search history.

(56) References Cited

U.S. PATENT DOCUMENTS

| 4,617,018 A | 10/1986 | Nishi |
| 4,685,921 A | 8/1987 | Peyman |

(Continued)

FOREIGN PATENT DOCUMENTS

| WO | WO2009/023774 A1 | 2/2009 |
| WO | WO2009/039315 | 3/2009 |

OTHER PUBLICATIONS

Adventus Technology, Inc., International Search Report and Written Opinion, PCT/AU2012/000290, dated Jun. 1, 2012, 17 pgs.
(Continued)

*Primary Examiner* — Niketa I Patel
*Assistant Examiner* — Nathan A Baldwin
(74) *Attorney, Agent, or Firm* — Jones Day

(57) ABSTRACT

A method for refilling a lens of an eye or increasing the elasticity of a lens of an eye includes removing a central portion of the lens core through the eye's cornea, a capsulorhexis in the eye's lens capsule and a gullet extending at least partially through the cortex of the lens. The lens is then refilled with a synthetic lens material. Sufficient lens core is left in place so that the synthetic material is not in contact with a lens capsule of the eye. The synthetic material used for refilling may be selected and may be formed in a shape and thickness so as to affect the refractive characteristics of the lens. An endocapsular lenticule may be inserted in the lens to affect the refractive characteristics of the lens.

23 Claims, 13 Drawing Sheets

(51) Int. Cl.
*A61F 9/007* (2006.01)
*A61F 9/00* (2006.01)

(52) U.S. Cl.
CPC ......... *A61F 2/1624* (2013.01); *A61F 9/00745* (2013.01); *A61F 2009/0087* (2013.01); *A61F 2009/00851* (2013.01); *A61F 2009/00889* (2013.01); *A61F 2009/00895* (2013.01); *A61F 2009/00897* (2013.01)

(56) References Cited

U.S. PATENT DOCUMENTS

| | | | |
|---|---|---|---|
| 5,807,401 | A | 9/1998 | Grieshaber et al. |
| 5,984,916 | A | 11/1999 | Lai |
| 6,322,556 | B1 * | 11/2001 | Gwon ..................... A61F 9/008 606/13 |
| 6,358,279 | B1 | 3/2002 | Tahi et al. |
| 6,399,734 | B1 | 6/2002 | Hodd et al. |
| 6,737,496 | B2 | 5/2004 | Hodd et al. |
| 6,744,197 | B2 | 8/2004 | Clayton et al. |
| 7,001,426 | B2 | 2/2006 | Lee et al. |
| 7,007,805 | B2 | 3/2006 | Hughes |
| 7,182,780 | B2 | 2/2007 | Terwee et al. |
| 7,348,022 | B1 * | 3/2008 | Clayton ................... A61L 27/18 424/422 |
| 7,452,377 | B2 | 11/2008 | Watling et al. |
| 7,655,002 | B2 | 2/2010 | Myers |
| 2003/0208265 | A1 * | 11/2003 | Ho ........................ A61F 2/1616 623/4.1 |
| 2006/0216329 | A1 * | 9/2006 | Peyman .................. A61F 9/008 424/428 |
| 2006/0271186 | A1 | 11/2006 | Nishi et al. |
| 2007/0173794 | A1 | 7/2007 | Frey et al. |
| 2009/0048586 | A1 | 2/2009 | Krueger et al. |
| 2009/0076602 | A1 | 3/2009 | Ho et al. |
| 2009/0137993 | A1 * | 5/2009 | Kurtz .................. A61F 9/00736 606/6 |
| 2009/0177189 | A1 * | 7/2009 | Raksi .................. A61F 9/00736 606/4 |
| 2010/0076417 | A1 * | 3/2010 | Suckewer ........... A61F 9/00838 606/4 |
| 2010/0191226 | A1 | 7/2010 | Blumenkranz et al. |
| 2010/0191230 | A1 * | 7/2010 | Dick .................... A61B 3/1005 606/5 |
| 2012/0026462 | A1 | 2/2012 | Uhlhorn et al. |
| 2012/0140173 | A1 | 6/2012 | Uhlhorn et al. |

OTHER PUBLICATIONS

Larkins, LenSx® Femtosecond Laser Receives 510(k) Clearance for Lens Fragmentation, www.lensxlasers.com, Apr. 27, 2010.

Palanker, Femtosccond Laser-Assisted Cataract Surgery with Integrated Optical Coherence Tomography, www.ScienceTranslationalMedicine.org , Nov. 17, 2010, vol. 2 Issue 58, pp. 1-10.

* cited by examiner

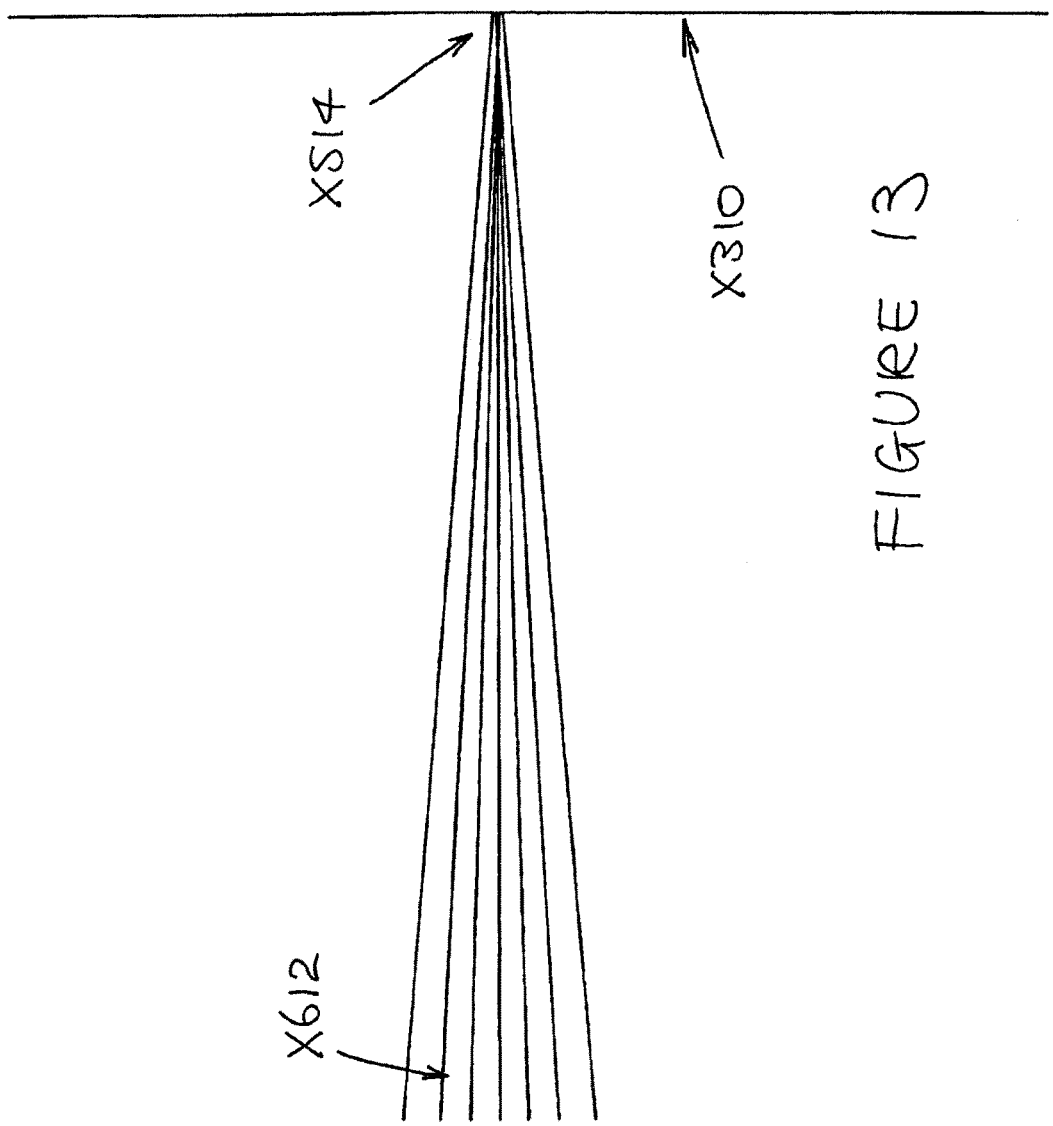

RESTORATION OF ACCOMMODATION BY LENS REFILLING

CROSS REFERENCE TO RELATED APPLICATIONS

This application is a United States National Stage Application filed under 35 U.S.C. § 371 of PCT Patent Application Serial No. PCT/AU2012/000290 filed on Mar. 20, 2012, which claims the benefit of U.S. provisional patent application No. 61/454,941, filed Mar. 21, 2011, the entire content of which is incorporated herein by reference.

FIELD OF THE INVENTION

The present invention generally relates to methods for performing medical procedures to the lens of an eye. Particular embodiments relate to a method and apparatus for restoring accommodation by lens refilling.

BACKGROUND OF THE INVENTION

Presbyopia is a condition where the eye exhibits a progressively diminished ability to focus on near objects due to a loss of elasticity of the crystalline lens. Apart from the application of corrective lenses, conventional treatment may also involve surgery. In such surgery, the first step is to make a corneal incision to form an opening to the anterior lens capsule with a process called capsulorhexis. After this the entire lens is removed, typically involving the emulsification of the lens using ultrasound, and then a synthetic intra-ocular lens (IOL) is inserted.

An alternative treatment is called the phaco-ersatz technique. The procedure involves the removal of the cortex and nucleus while preserving the lens capsule and its zonular attachments. The empty lens capsule is then refilled with biocompatible and optically suitable clear gel. The phaco-ersatz technique involves the removal of as much of the lens core and lens epithelial cells (LEC) as possible with the aim of (1) maximising accommodative outcome; and (2) eliminating LEC, the source of posterior capsular opacification (PCO) which is an adverse effect associated with intracapsular surgery including cataract with IOL implantation. PCO can degrade vision to the point when ophthalmic surgical intervention is required. Aspirators and phaco-emulsification probes (or "phaco-probe") are used to remove the entirety of the lens core and LEC.

A number of advances have been made in the phaco-ersatz technique. For example, in one improved technique the hardened core (cortex and nucleus) of a presbyopic lens is first removed using a procedure modified from the extracapsular cataract extraction (ECCE) procedure; the main modification being the evacuation of lens material via a peripheral, mini-capsulorhexis. The patency of the capsule is maintained during this procedure. Following extraction of the lens core, a synthetic material, usually a polymer gel with the appropriate physical (mechanical and optical) properties, is used to refill the capsule via the mini-capsulorhexis.

Further enhancements include the use of improved polymer gels for restoring accommodation in presbyopes, as well as the use of a valve for sealing the capsulorhexis (or capsulotomy).

Despite advances made in the available polymer gels and the procedure, there are still some challenges to achieving a clinically acceptable end-product, for example:

Despite the removal of almost all LEC in the procedure, PCO (the unregulated proliferation of LEC causing severe loss of visual quality) continues to be a problem to medium/long-term success.

In order to eliminate as much LEC as possible, in a conventional cataract operation, an irrigation and aspiration (I/A) probe is used to remove the lens cortex and the tip of the I/A probe will be in direct contact with the capsule when removing the LEC from the anterior part of the capsule. The risk of capsule rupture is substantial. Rupture can be caused by the inadvertent application of direct suction on the internal capsule surface due to an accidental misplacement of the aspirator or phaco-probe tip. A rupture of the capsule renders the lens ineligible for phaco-ersatz with a polymer gel and a more conventional treatment (e.g. IOL) is required. The patient thereafter cannot enjoy the benefits of high amplitude, continuous focus accommodation made possible by lens refilling.

The physical property of the polymer gel is such that it is difficult to fill the capsule to the lens equator. Typically, a 'void' remains which (1) presents a site for LEC proliferation and PCO; (2) reduces mechanical coupling between the intracapsular gel and the equatorial lens capsule which reduces the efficiency and efficacy of mechanical accommodation.

For some versions of the polymer gel, irradiation directed through the dilated pupil is required to cure (photo-crosslink) the gel. Since the iris overhangs the lens regardless of levels of mydriasis, gel lying at the peripheral, near-equatorial regions of the lens often does not receive sufficient radiation and becomes under-cured or remains uncured. This presents a greater risk for post-operative leakage of gel into the eye, increasing the potential for ophthalmitis and other complications.

In addition to suffering from presbyopia, a person may also be experiencing refractive error. For example, a presbyope may also be a myope (individual short-sightedness) or a hyperope (individual with long-sightedness) or an astigmat (individual with astigmatism).

SUMMARY OF THE INVENTION

Embodiments of the invention generally relate to a method of lens refilling and may be used for treating presbyopia. From one perspective, the invention may be viewed as building on the phaco-ersatz technique. The method includes removing and refilling only a portion of the lens core, not the entirety of the lens core.

Embodiments of the invention generally relate to surgical alteration of the refractive properties of the lens of an eye. The alteration of the refractive properties may be performed simultaneously with the treatment of presbyopia. The optical properties and volume of material used to refill the lens are selected to affect the refractive properties of the lens. In this way refractive error in the eye may be at least partially corrected.

Embodiments of the invention generally relate to a device for use in a lens refilling surgical operation and to machine readable instructions for controlling such a device. The device is controlled to facilitate removal of only a portion of the lens core, as opposed to the entirety of the lens core.

A method for refilling a lens of an eye includes removing a central portion of the lens core through the eye's cornea, a partial capsulotomy or capsulorhexis in the eye's lens capsule and a gullet extending at least partially through the cortex of the lens. The lens is then refilled with a synthetic lens material.

A method for increasing elasticity of the lens of an eye includes removing a central portion of a lens core of the eye and refilling the central portion with a replacement synthetic material of higher elasticity than the removed central portion of the lens core. Sufficient lens core is left in place so that the synthetic material is not in contact with a lens capsule of the eye.

The synthetic material used for refilling may be selected and may be formed in a shape and thickness so as to affect the refractive characteristics of the lens, having regard to the refractive index of the synthetic material. Similarly, the synthetic material used may be selected having regard to the refractive index that provides the required refractive characteristics of the lens after surgery, having regard to the shape of the lens material that will be formed by filling the void. In this way, for example, myopia or hyperopia may be partially or fully corrected by the optical properties of the synthetic material. Astigmatism, spherical aberration and higher order aberrations may also be modified by optical properties of the synthetic material in combination with the power of the remaining lens tissues.

An endocapsular lenticule may be placed against, attached to or inserted into a portion of the lens core that was not removed. The endocapsular lenticule may be designed to affect the refractive characteristics of the lens. The effect on refractive characteristics of the lens may be in addition to any effect the optical properties of the synthetic refilling material has and may supplement the optical properties of the synthetic refilling material when they are favourable or at least partially correct optical properties of the synthetic refilling material when they are unfavourable.

Further aspects of the present invention and further embodiments of the aspects described in the preceding paragraphs will become apparent from the following description, given by way of example and with reference to the accompanying drawings.

BRIEF DESCRIPTION OF THE DRAWINGS

FIG. 13 shows a highly magnified view of the light rays near the focus of the eye following treatment of FIG. 12.

DETAILED DESCRIPTION OF THE EMBODIMENTS

Figure 1:
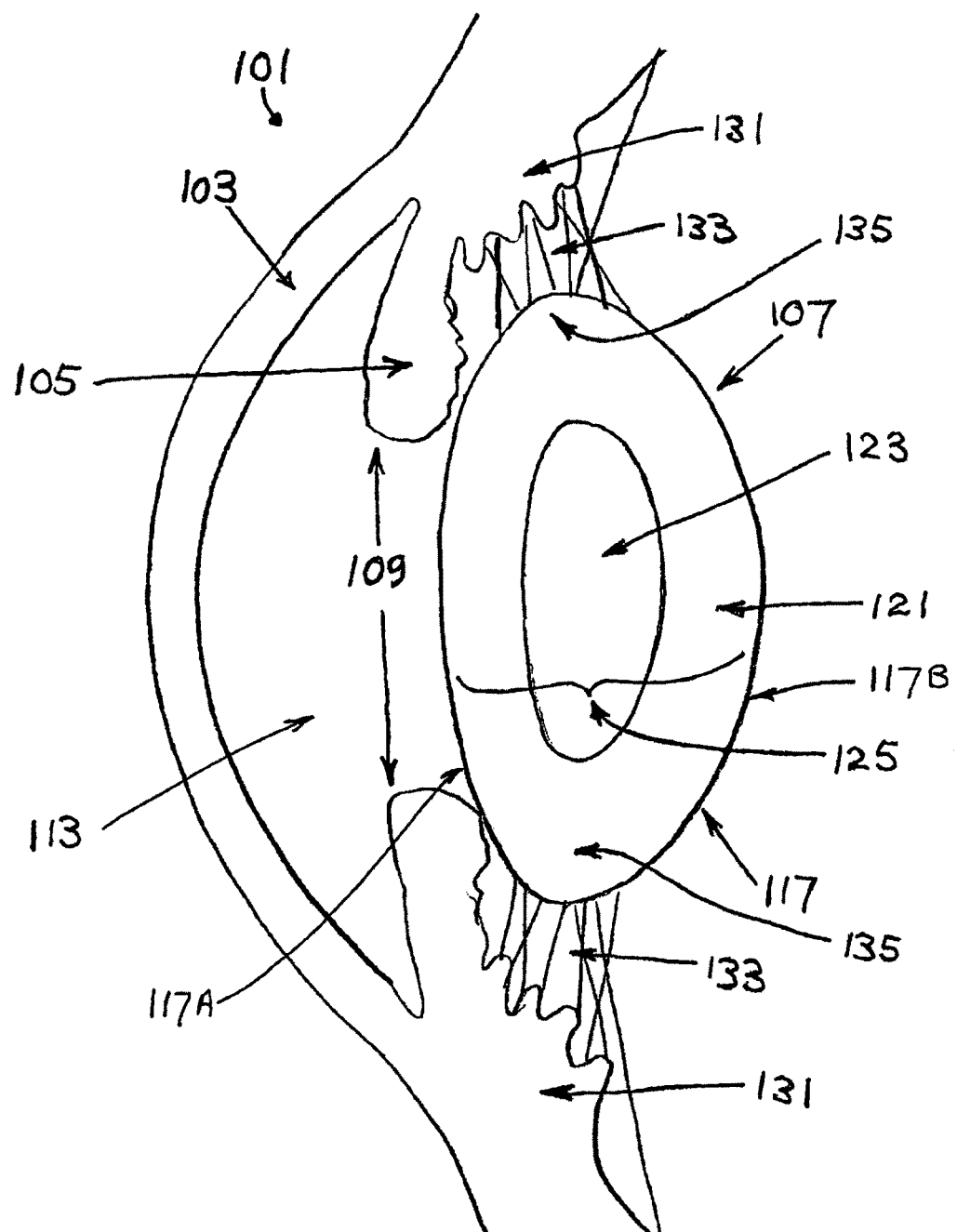
FIG. 1 shows a section through an eye including representations of the cornea and lens.

FIG. 1 shows an anterior segment of an eye 101, which includes a cornea 103, an iris 105 and a lens 107. In FIG. 1, the front of the eye 101 is to the left. Light travels into the eye from left to right. The anterior-most component of the eye 101 is the cornea 103. Behind the cornea 103 is the anterior chamber 113. The anterior chamber 113 is bounded posteriorly by the iris 105 and the anterior surface 117A of the capsule 117 around the crystalline lens 107 (or just "lens"). The opening defined by the iris 105 is the pupil 109 of the eye. Surgical operations carried out intraocularly, including on the lens 107 are often reliant on visualisation of the procedure through the cornea 103 and the pupil 109.

The components of the lens 107 include the capsule 117 surrounding the lens core 125 consisting of the central nucleus 123 and a cortex 121 outside of the nucleus. The lens 107 may be thought of as possessing a few subcomponents. Firstly, the capsule 117 is an elastic membrane that surrounds the core 125 of the lens 107. The capsule inner surface is populated by a single layer of cells, called lens epithelium cells (LEC). The anterior capsule 117A is adjacent to the anterior chamber 113 while the posterior capsule 117B lies towards the more posteriorly located vitreous of the eye (not shown). Secondly, the core 125 (the entirety of the internal contents encased by the capsule 117) of the lens 107 is divided into a central nucleus 123 and the cortex 121 surrounding the nucleus 123. The lens 107 is suspended by thin zonules 133 which are attached to the ciliary body 131. These features are located beyond the periphery of the lens 107 and behind the iris 105.

Together, the cortex 121 and nucleus 123 comprise the lens core 125. According to accepted theories of accommodation, change in the lens shape during accommodation is effected by forces acting from the ciliary body 131, via the zonules 133 and on through to the lens capsule 117 at the equatorial region 135.

Figure 2:
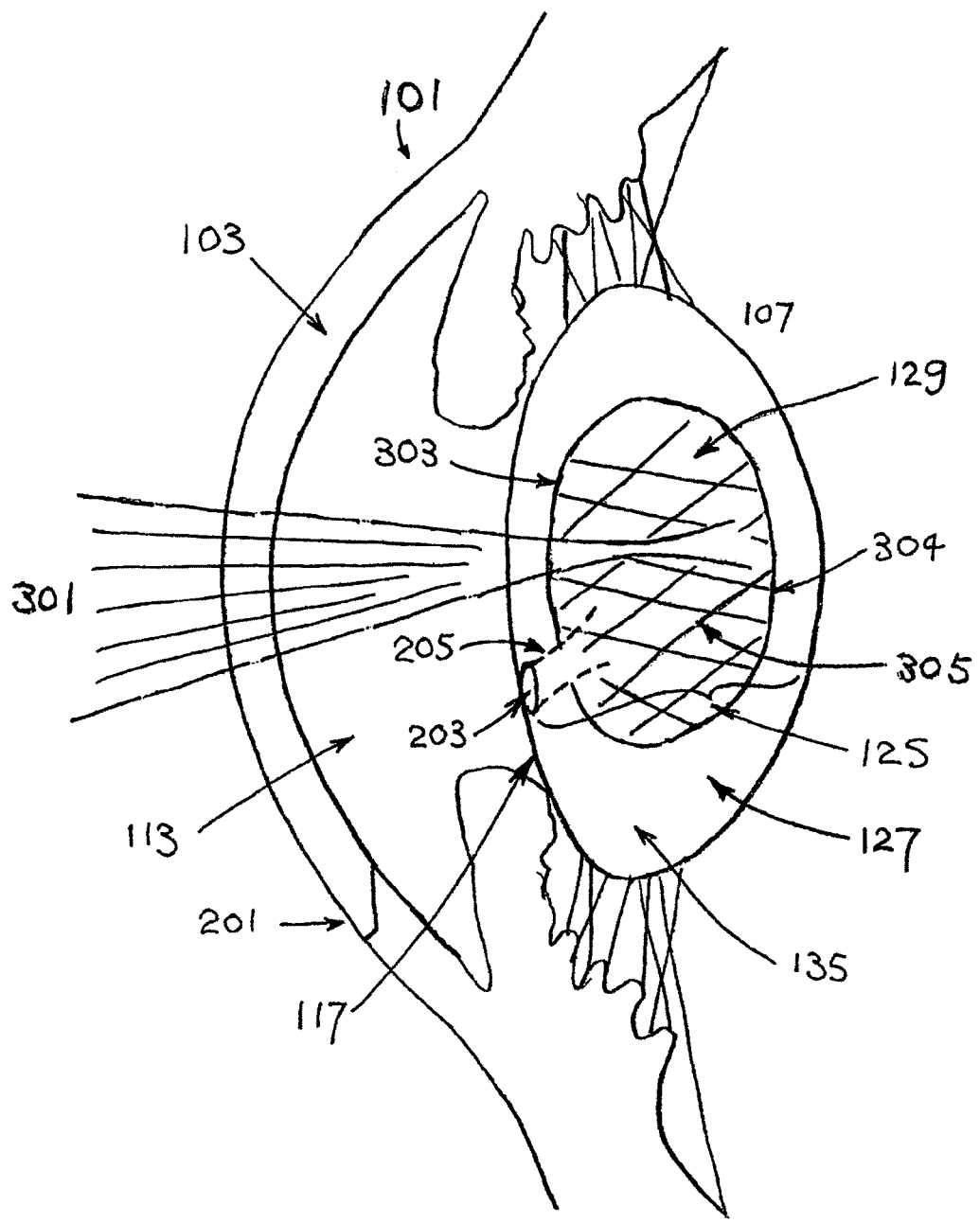
FIG. 2 shows the section through the eye of FIG. 1 including ablations formed in the core of the lens, a gullet, a partial capsulotomy or capsulorhexis and corneal incisions.

In FIG. 2, preparatory ablations of the central lens core 129 are shown. The preparatory ablations assist to allow removal of the central lens core 129 while leaving the more superficial layers 127 in place. In some implementations of the method, the central lens core 129 may be approximately coincident with the central nucleus 123. However, in other implementations the central lens core 129 may cover more or less of the lens core 125 than the central nucleus 123. In the currently preferred embodiment, the central nucleus 123 is removed in its entirety and a central portion of the cortex 121 is also removed.

For many patients, the thickness of the lens nucleus at the age when presbyopia sets in is around ½ (one-half) to ⅔ (two-thirds) of total lens thickness. In some embodiments, the goal core to be removed may include the entirety of the lens nucleus, so that for at least these patients, a minimum volume to remove (i.e. only the lens nucleus) would be around 12.5% to 30% of total lens volume. The remaining volume is dependent on the thickness of the cortex that is to be left intact as well as dependent on average lens dimensions. Selection of the thickness of the cortex that needs to be left intact may be made with reference to the LEC. The LEC are about 10 µm to 15 µm thick on the anterior capsule and there are none on the posterior capsule.

The maximum amount of cortex removed may be selected having regard to the objective of leaving the LEC intact.

Accordingly, where the amount of lens core removed is to be maximised, between 10 μm to 50 μm thickness core is left over the LEC. Selection of the thickness of the anterior cortex that is intended to be left in place may be made having regard to the precision of the laser being used. A typical laser precision is approximately 15 μm. For this reason, or to provide some additional tolerance for maintaining the LEC, in some embodiments the goal anterior cortex thickness may be a value selected from the range 25 μm to 75 μm.

Because LECs at the equatorial region 135 of the lens are longer, a greater amount of the cortex may be left in place in this region. For example, performing a cut leaving at least 250 μm of the LECs and cortex in the equatorial region 135 of the lens may be appropriate. In some embodiments, the shape of the cut at the equatorial region 135 is cylindrical.

Although there may at times be no or very few LECs adjacent the posterior capsule, LECs do proliferate and migrate and may also do so along the posterior capsule. Consequently in some embodiments natural cortex material is left adjacent the posterior capsule. For example, a minimum thickness of cortex to leave adjacent the posterior cortex may be selected from the range 15-20 μm, reflecting the aforementioned laser precision. If a laser with higher precision is used, the minimum cortex may be less than 15 μm, for example 10 μM. In other embodiments, a minimum thickness of cortex to leave adjacent the posterior cortex may be 30 μm. Leaving cortex material adjacent the posterior capsule also reduces the risk of capsule rupture. In some embodiments, the thickness of cortex left adjacent the posterior cortex is selected to be the same as the thickness left adjacent the opposing anterior capsule. In other embodiments, the thickness profile is asymmetrical. In some asymmetrical embodiments, more cortex may be left adjacent the anterior capsule than the posterior capsule. In other embodiments, particularly those where a supplementary endocapsular lenticule (see herein below) is to be inserted in the posterior lens, then more cortex may be left in the posterior capsule to receive the lenticule periphery.

Where the structure of the eye is known, for example where a surgeon is able to distinguish between an outer cortex where the cortex remains soft, and a more central cortex that may not remain soft but may harden to some degree, then the nucleus will be removed together with the more central cortex, leaving the soft outer cortex intact before refilling the lens.

In this example, a suitably programmed femtosecond-laser (fs-laser) delivers a beam 301 into the central lens core 129. Generally, a laser operating at below about 1 picosecond light pulse at 50% bandwidth is called a fs-laser. A fs-laser for laser phacofragmentation during cataract surgery has been reported as approved by the United States FDA by LenSx Lasers, Inc of Aliso Viejo, Calif., USA. The use of a fs-laser for disruption of tissue is described in international patent application PCT/US2008/073154 (Krueger et al), published as international publication number WO 2009/023774 A1, the entire content of which is hereby incorporated herein by reference. Laser ablation of a lens for cataract surgery is described in U.S. patent application Ser. No. 12/510,148 (Blumenkranz et al), published as US 2010/0191226 A1, the entire content of which is hereby incorporated herein by reference. This type of laser ablation is a suitable technique to use in the method as described herein. Although the laser device described herein is called a fs-laser, those skilled in the relevant arts will appreciate a range of laser devices that may be utilised for the purposes of the present invention.

A suitable scanning algorithm programmed into the fs-laser delivers an anterior bounding ablation 303 and a posterior bounding ablation 304 as well as 'chopping' ablations 305 in the region between the anterior bounding ablation 303 and the posterior bounding ablation 304.

The bounding ablations anteriorly 303 and posteriorly 304 describe ('mark out') the extent of the central lens core 129 to be extracted, separating the central lens core 129 to be extracted from the more superficial layers 127 of the lens core 125, thereby assisting to prevent inadvertent removal of material from the more superficial layers 127 during extraction. The 'chopping' ablations 305 section the central lens core 129 into small fragments to facilitate rapid and uneventful removal during extraction of material from the central lens core 129.

The fragments resulting from the chopping ablations 305 may be cuboids or quazi-cuboids with sides ranging in length from 200 μm to 1 mm depending on the speed (pulse/second) of the laser used. For a harder nucleus, a smaller fragment size is preferable. However, from the delivered energy point of view, the larger the fragments, the less energy is used, the better for the eye from the thermal and radiation safety standpoint. Accordingly, in a method of surgery, the hardness of the nucleus is evaluated and the cut size selected dependent on the hardness of the nucleus.

To overcome difficulties caused by optical scattering introduced by laser ablation (e.g. due to cavitation bubbles caused by the laser as well as the loss of transparency in the lens substance as a result of ablation) typically the ablations described-above with reference to FIG. 2 are executed in a postero-anterior direction (i.e. from tissues nearer the retina towards tissues nearer the cornea) as well as from peripherally to centrally. Thus, when implemented using a fs-laser, the posterior bounding ablations 304 would be effected first; followed by the chopping ablations 305; then the anterior bounding ablations 303.

One or more corneal incisions 201 are created by the surgeon in the cornea 103 to provide access to the anterior chamber 113 and lens 107. These corneal incisions may include, for example, a first corneal self-sealing incision (often introduced for the anterior chamber maintainer-BSS line to prevent eye collapse), and a second corneal self-sealing incision (for irrigation, aspiration and the injection cannula). As the making and purpose of the first corneal incision is known, further details are provided below of only the utilisation of the second corneal incision.

A capsulorhexis 203 is created on the lens 107 through the lens capsule 117. The opening on the lens 107 may be created manually by tearing the lens or through use of a cutting instruments, for example a fs-laser, in which case the opening may instead be called a capsulotomy. For clarity of description, for the remainder of this specification the opening is called a capsulorhexis regardless of whether it is created by tearing or using a cutting instrument. A tubular channel or gullet 205 is created leading from the capsulorhexis 203 and through the more superficial layers 127 of the lens core 125 and into the more central lens core 129. The capsulorhexis covers about 270 to 330 degree of the circumference, leaving a capsule tag that will hold the cut capsule flap (not shown in the figures) and about 100 to 500 μm of the tissue beneath that will comprise the intact epithelium and cortex. After refilling, the capsulorhexis will then be closed my merely replacing the flap over the gullet made in the lens. As the LECs have not been damaged, they will migrate and seal the gap.

The corneal incision(s) 201, capsulorhexis 203 and gullet 205 may be made via any suitable technique. For example, the surgeon may create these manually using their selected cutting instruments, forceps and any other devices using techniques currently used for inserting intraocular lenses into the lens capsule 117. In alternative embodiments the capsulorhexis 203 and/or gullet 205 are created with the assistance of the fs-laser.

If needed, the capsulorhexis 203 can have installed a sealing valve as disclosed in U.S. Pat. No. 7,182,780, U.S. Pat. No. 7,001,426 or U.S. Pat. No. 6,358,279, incorporated herein by reference as far as they are consistent with this description.

If the fs-laser is used to assist in the creation of the capsulorhexis 203 and gulleting 205, then these would be created after the anterior bounding ablations 303. As explained, the more posterior 205 gulleting may be created or defined by the fs-laser before the capsulorhexis 203. If the capsulorhexis 203 and gulleting 205 are created manually by a surgeon, then the surgeon may defer this until after the fs-laser has been applied to the lens core 129.

Figure 3:
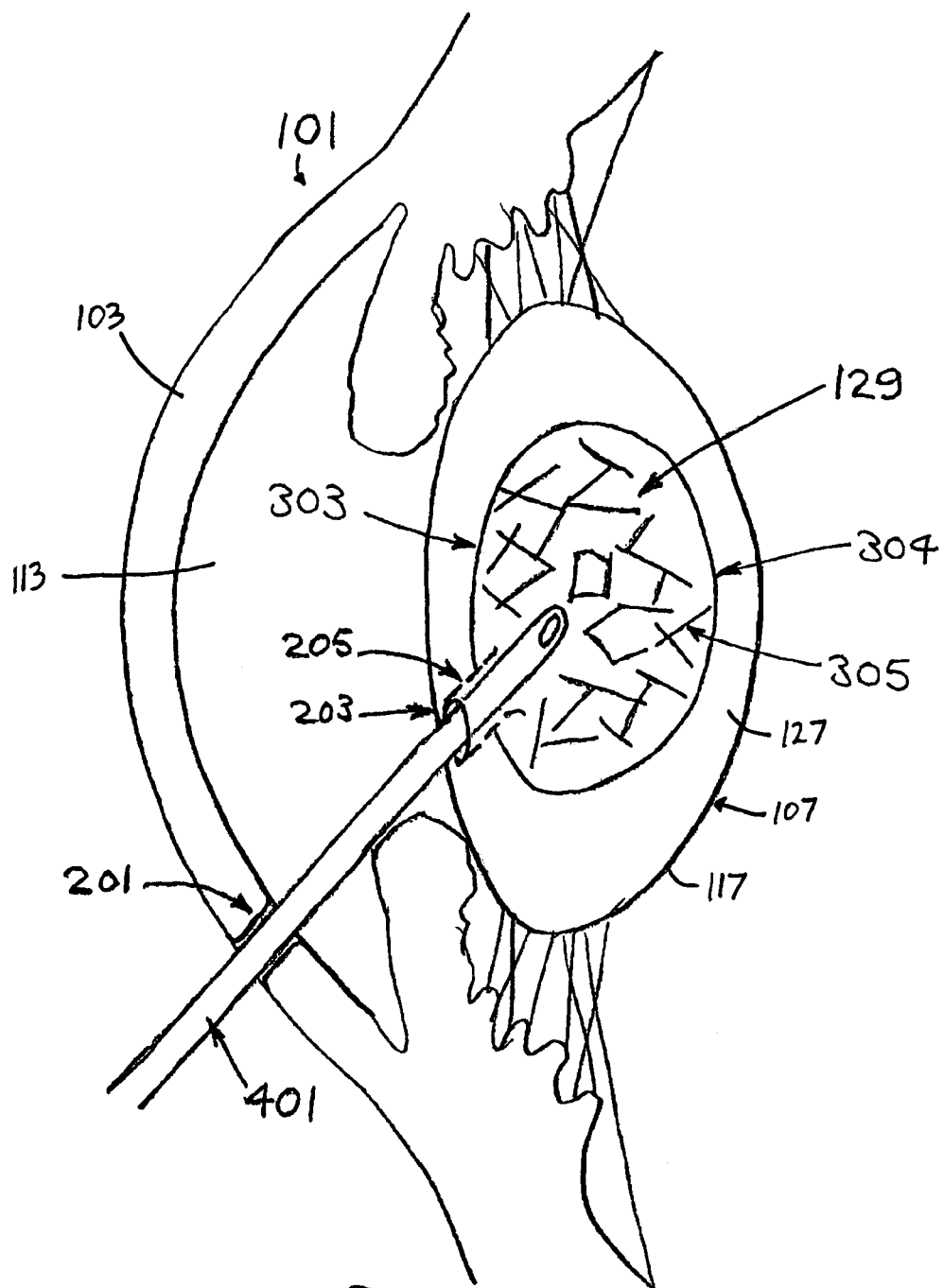
FIG. 3 shows the removal of the ablated core.

In FIG. 3, material from the central lens core 129 is extracted via the superficial cortex gullet 205, the capsulorhexis 203 and the corneal incision 201. Extraction may be effected using any suitable cataract surgery implement 401 including aspirators and phaco-emulsification probes. As explained, the preparatory ablations may facilitate this process. In alternative embodiments the central lens core 129 may be removed without first creating all of the anterior bounding ablation 303, posterior bounding ablation 304 and 'chopping' ablations 305. In these embodiments, the surgeon removes only the central lens core 129 despite the lesser number of preparatory ablations.

Figure 4:
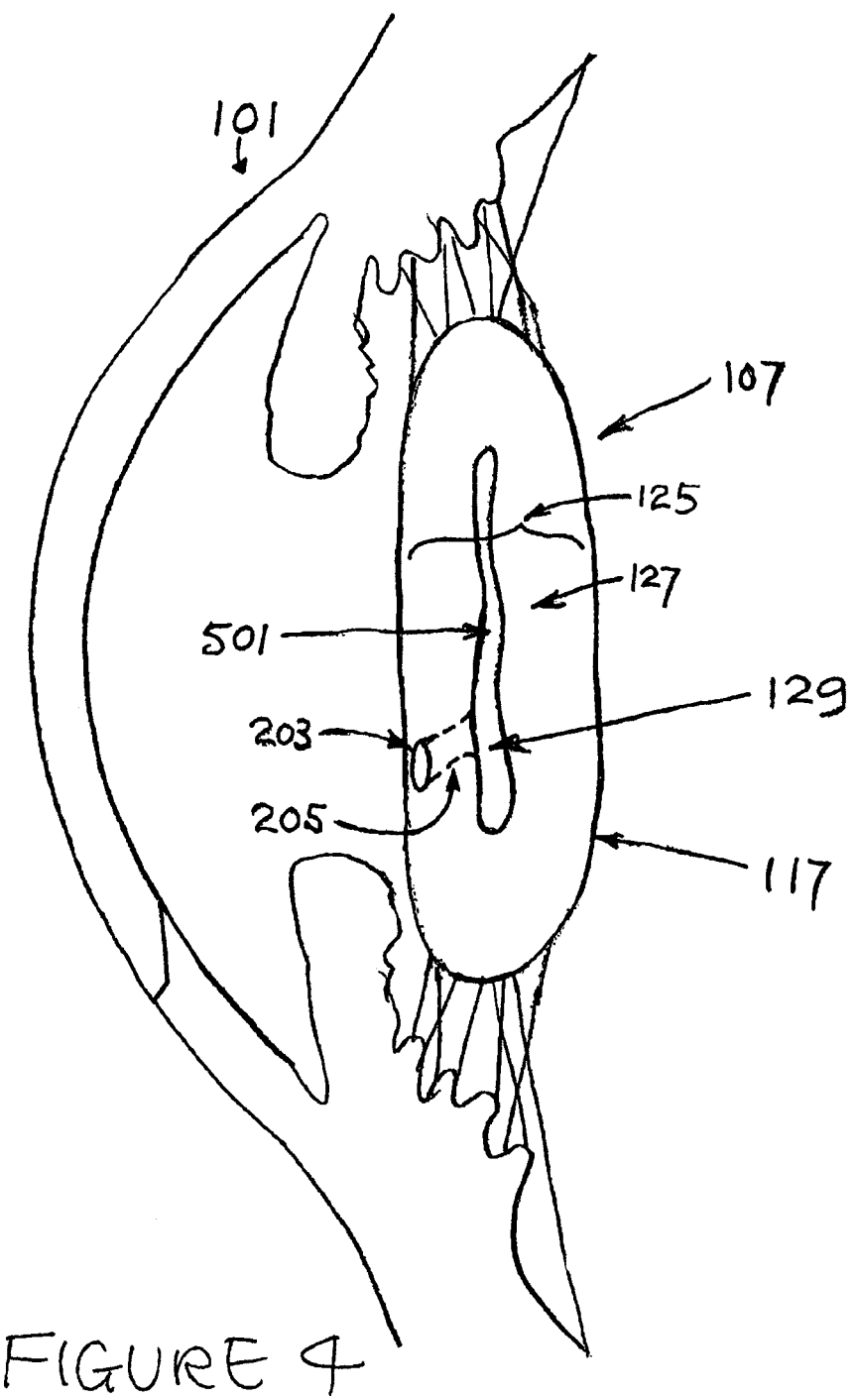
FIG. 4 shows the eye with the lens collapsed following removal of the ablated core.

FIG. 4 shows the lens 107 following extraction of material from the central lens core 129. The void volume 501 (partially collapsed due to the absence of lens core material) is left following extraction. Other than the introduction of the capsulorhexis 203 and superficial cortex gullet 205, the capsule 117 and the more superficial layers 127 of the lens core 125 remain intact.

Figure 5:
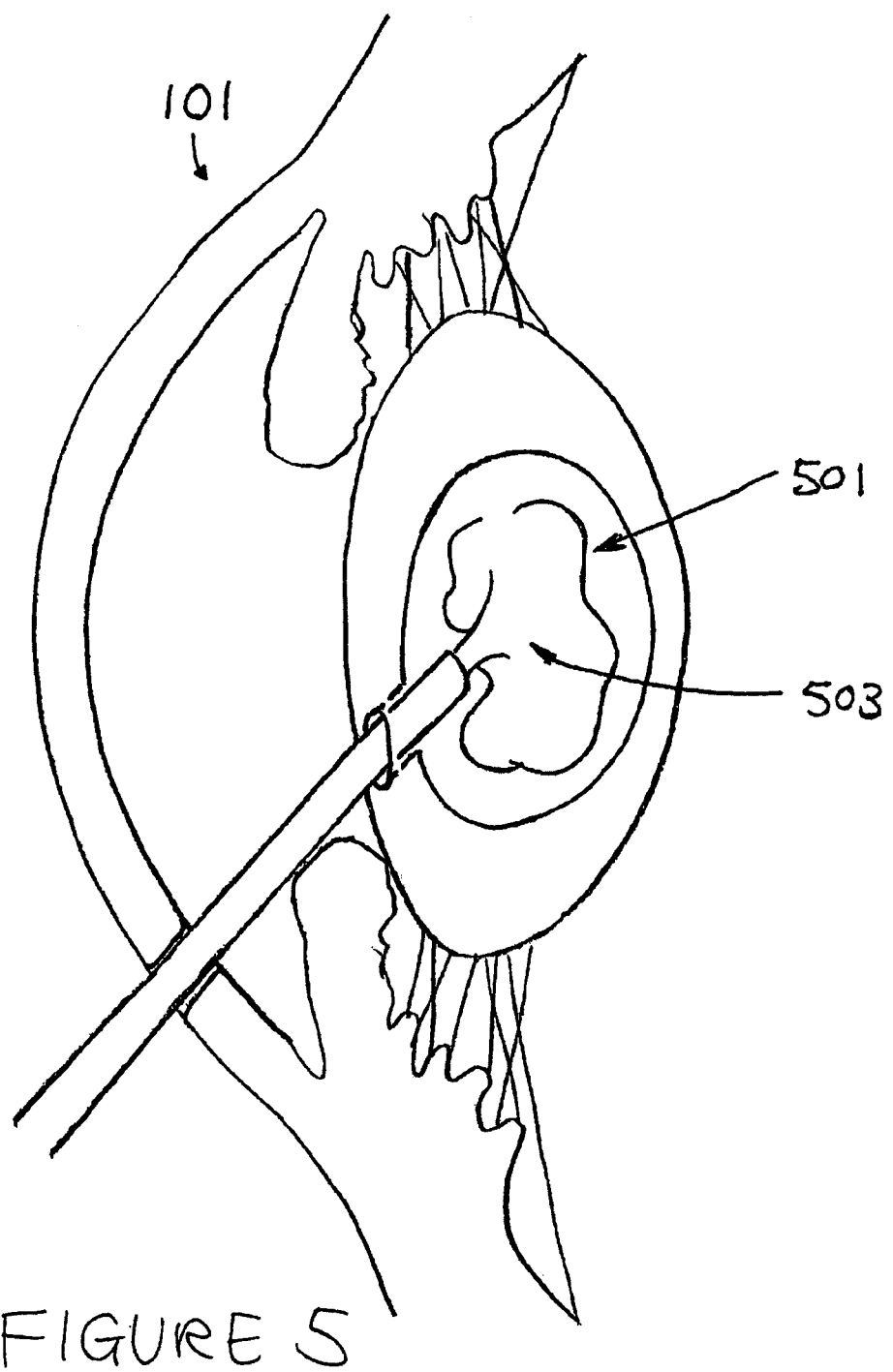
FIG. 5 shows the refilling of the lens with a polymer gel.

FIG. 5 shows the process whereby the void volume 501 created as a result of the extraction process is refilled with an appropriate material 503. This may be a synthetic material such as a polymer gel-type material with appropriate mechanical and optical properties to restore the static and dynamic (i.e. during accommodation) optical properties of a younger, pre-presbyopic lens. The gel-type materials and refilling techniques may be any material and technique known to be suitable for the phaco-ersatz technique.

Examples of types of gel that can be used include siloxane (polysiloxane) and hydrophilic gels as described in any of the following patents, all of which are incorporated herein by reference: U.S. Pat. No. 7,452,377, U.S. Pat. No. 7,348,022, U.S. Pat. No. 7,007,805, U.S. Pat. No. 6,774,197, U.S. Pat. No. 6,737,496, U.S. Pat. No. 6,399,734. Silicone oils, such as trimethyl terminated dimethyl-siloxane (n=~1.403) of the correct viscosity is also suitable, although due to the refractive index of silicone oil it is preferably used in combination with an endocapsular lenticule.

Figure 6:
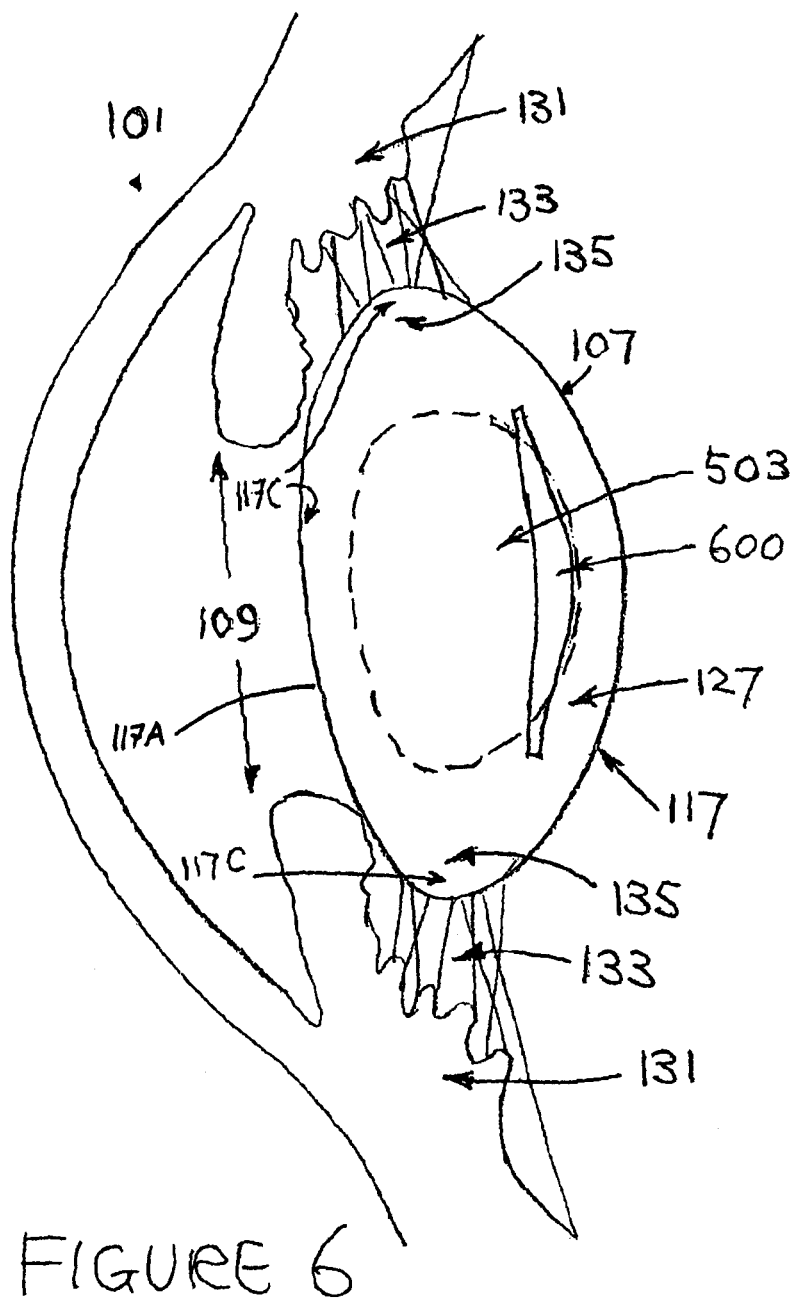
FIG. 6 shows the eye following the lens refilling and with endocapsular lenticule in place.

FIG. 6 shows the eye 101 and lens 107 following lens refilling. The refilling gel 503 is located only at the centre of the lens 107. It is neither in contact nor in close proximity to the lens capsule 117. This means that LEC 117C, which originates from the lens equatorial region 135 and propagates to lie along the internal surface of the capsule 117 and more particularly the anterior capsule surface 117A, remains in tight contact with the natural superficial layers 127 of the lens core 125 and does not experience the stimulus for unregulated proliferation. Due to its central placement (both axially and radially), the entirety of the gel 503 lies away from the equatorial region 135 of the lens 107 but still in direct contact with the cortex 127 at the equatorial region 135. This means that continuity of mechanical coupling is maintained from the ciliary body 131, via the zonules 133 and the capsule 117 at the lens equatorial region 135, and on through the lens cortex 127 at the lens equatorial region 135 and ultimately the gel 503. The continuity of mechanical coupling may, for some patients, provide improved mechanical accommodative efficiency.

When using photo-cured gels it is advantageous for the gel 503 as seen through the pupil 109 to be slightly larger than the largest natural pupil size in a darkened room. This will ensure uniform optical effects across the entire pupil allowing for good quality, unaberrated vision. In other embodiments, the gel 503 may be comparable in size to the natural pupil size in a darkened room, for example the same size or only slightly smaller. Even when the gel 503 is slightly larger 10, than the pupil size, because the curing light beam is able to diverge slightly to spread slightly behind the iris (depending on the numerical aperture of the curing light source), irradiation applied for curing will reach the entirety of the gel 503 eliminating the potential for under-cured or uncured gel, which represents a biocompatibility hazard.

On the other hand, since the lens diameter is greater than the pupil diameter, for non-photocured gel the only limitation is for the gel to be not contacting the capsule, specifically at the equator.

Also shown in FIG. 6 is an endocapsular lenticule 600, which in some embodiments is inserted into a portion of the lens core. In other embodiments the endocapsular lenticule 600 is omitted. Further details of the methods by which an endocapsular lenticule 600 may be provided are described below.

Figure 7:
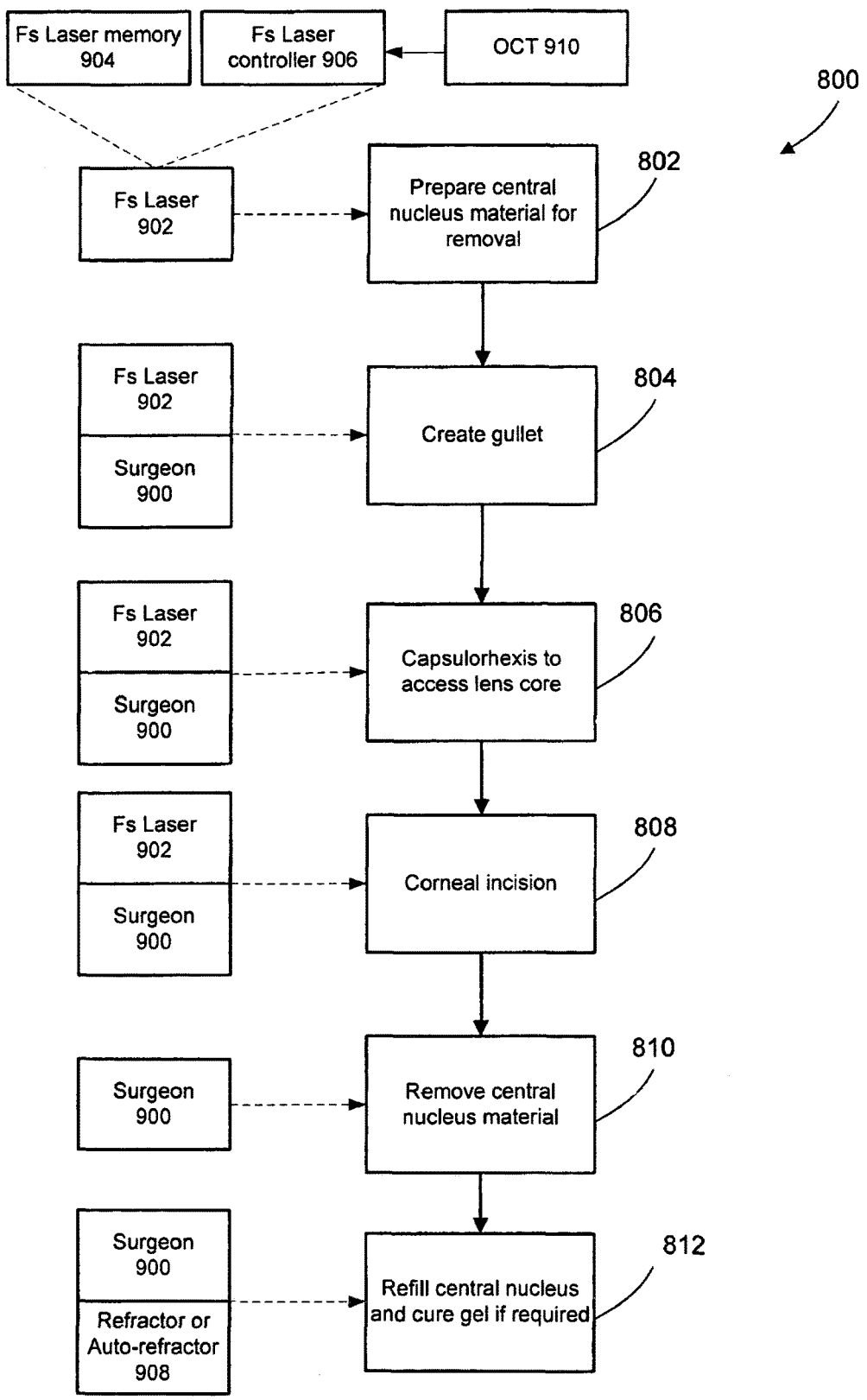
FIG. 7 shows a flow-diagram of the method steps represented in FIGS. 2 to 6.

FIG. 7 shows a method 800 of refilling the lens 107. The method steps are shown to the right of FIG. 7 and options for performance of the respective method step are shown to the left. These options are the surgeon 900 only (using appropriate surgical tools for the task), the programmed fs-laser 902 only, or either the surgeon 900 or the fs-laser 902. Steps described herein as being performed by the surgeon are intended to include steps performed by robotic surgeons, either controlled by a human surgeon physically located near or remote to the robotic surgeon and to the robotic surgeon performing actions automatically.

At step 802 the core material is prepared by the fs-laser 902 for selective removal. This includes making anterior bounding ablation 303 and the posterior bounding ablation 304. Optionally, this step may also include the ablation of the central nucleus material by 'chopping' ablations 305. As explained, the non-contact, non-invasive fs-laser may be used for the ablation of ocular tissues. In such cases, the fs-laser may be programmed to create an 'entrance-less' pre-sectioning ablation of the lens core to pre-describe the extent of the lens core to be extracted and to facilitate removal of the target portion of the lens core. The programming to create the ablation may be stored in memory 904, readable by a controller 906 of the fs-laser 902.

As explained, the use of an fs-laser for ablation of lens tissue as described above may require a strict order of ablation due to optical scattering (caused by cavitation bubbles as well as a loss in transparency of the ablated tissues) created by the process of laser ablation that interferes with the efficacy of laser ablation. In general, the ablation algorithm should proceed from the more posterior layers to the more anterior layers and from the peripheral to the central regions. For example, an example algorithm which includes the creation of the capsulorhexis 203 and corneal incision 201 by the laser, entails the following:

(i) create the posterior bounding ablation 304 up to approximately the equatorial region 135 by scanning the laser across the lens, (ii) create the 'chopping' ablations 305, from the back to the front, optionally starting with the most posterior peripheral ablations, followed by the central ablations, and (iii) create the anterior bounding ablation 303, starting at the periphery and working towards the centre.

As explained, the fs-laser may also be used to create one or more of the gullet 205, capsulorhexis 203 and incision(s) 201. In these embodiments, the algorithm may continue with instructions to cause the fs-laser to:

(iv) form the tubular channel or gullet 205 in a postero-anterior direction (step 804), (v) create the capsulorhexis 203 (step 806), (vi) create a first corneal self-sealing incision 201, for anterior chamber maintainer-BSS line to prevent eye collapse (step 808), and (vii) create a second corneal self-sealing incision 201, for aspiration and injection cannula (step 808).

The fs-laser may be guided by the use of imaging systems such as an optical coherence tomography (OCT) system 910 (see FIG. 7), that provide images for planning the ablation. A closed-loop or semi-closed loop system may be used for guiding the ablation systems. In some embodiments, the ablations are formed using real-time, direct imaging of the lens simultaneous to laser ablation. The OCT system can image a cross-section of the lens or the whole lens in 3D, thus providing the precise location of the anterior/posterior capsule and nucleus.

Where the OCT system has a shallow depth range that cannot cover the whole anterior segment and the crystalline lens, then an image is taken of the cornea and iris and another of the lens. These two images are stitched together to get distances from the cornea to the anterior and posterior lens capsule. The laser cutting depth is then programmed in the PC controlling the fs-laser. However this is done before surgery and therefore any changes that might occur, such as intraocular pressure (IOP) reduction due to excessive manipulation of the eye before surgery, could cause the cut to be displaced in the vertical direction. In addition, some fs-lasers locate the laser with reference to the corneal apex and assume a particular curvature of the lens. However, the anterior and posterior curvatures of the lens capsules are not all the same in all people. To avoid iatrogenic capsule damage using OCT systems with these limitations, a safety margin of about 500 μm may be included from both the posterior and anterior capsule. In older people, the cortex might be thinner than 500 μm, these lasers will only chop the central nucleus, leaving some of the nucleus in place. As the nucleus material is much stiffer than the cortex, the amount of accommodation restored will be less.

To remove all or at least more of the nucleus below the anterior capsule and above the posterior capsule, a more precise instrument may be required, that would allow cutting with a safety margin of about 100 μm or less to both capsules.

To reduce the safety margin an instrument capable to trace the patient's capsule in real time is used. This will allow full use of the fs-laser precision, which may be about +/−5 μm or about 10 μm total error). A suitable OCT system and method is disclosed in U.S. patent application No. 61/369,269 and/or U.S. patent application Ser. No. 13/194,067 (published as US 2012/0026462 A1) and/or U.S. patent application Ser. No. 13/309,374 (Uhlhorn et al), the entire content of each of these applications is hereby incorporated herein by reference. In one embodiment, the above mentioned OCT system is used to provide in real time optical surfaces of the anterior segment of the eye including measurements selected from the group: the cornea anterior and posterior curvatures and its thickness; the anterior chamber depth (distance between the posterior corneal surface and anterior capsule surface of the lens); the position of the iris plane with respect to the cornea outer surface; the diameter of the pupil; the anterior and posterior curvatures of the lens capsule; the positions of the anterior and posterior lens capsule surfaces with respect to the corneal outer surface and/or the outer boundaries of the nucleus and their positions with respect to the anterior and posterior capsule surfaces. As all distances are extracted from the same OCT scan in real time, all can easily be related to a common geometric reference: for example the outer surface of the cornea. Using the outer surface of the cornea as the common geometric reference may be particularly appropriate when using an f-s laser that uses a contract glass that locks on the outer corneal surface of the patient.

The data gathered by the above mentioned OCT system is processed by a microprocessor that supplies to the computer controlling the fs-laser (if different from the microprocessor processing the data gathered by the OCT system) to tridimensional X-Y-Z coordinates as to where to cut.

The position of the crystalline lens with respect to the cornea is function of the patient's IOP. The 10P may vary due to anaesthetics, pressurizing the cornea by manipulation of the globe or by placing a contact glass (such as those used with some f-s lasers) against the cornea. Minimising the IOP variation may therefore maximize the precision of the laser surgery. Accordingly, in some embodiments the surgical steps are performed with a closed eye (=no openings, no aqueous fluid egress, no undue pressure on the globe and no undue pressure on the cornea). Therefore, after cutting the nucleus, cutting the walls of the gullet and performing the partial capsulotomy, two non-perforating incisions are made in the patient's cornea from back to front, thus leaving the cornea's Bowman's layer and the cornea's epithelium intact. In such a case, the internal geometry of the eye is maintained intact during the whole f-s laser procedure.

Alternatively, one or more of steps 804 to 808 are performed manually by the surgeon using known techniques.

At step 810 the core material of the lens 107 is removed such that only the more centrally located core 129 material is removed while the core material adjacent to or in near proximity to the capsule surface is left intact. Extraction of the target portion of the lens core is effected via the capsulorhexis 203 and corneal incision/s 201 created in steps 802 and 804. This step differs from that of the conventional phaco-ersatz method in that only the more centrally located lens core 123 is removed—leaving the lens cortex 121 tissue in direct contact or near proximity to the lens capsule 117 (around the entire three-dimensional surface boundary of the capsule) intact.

Refilling of the more central void volume as shown in FIG. 5, created by the removal of the more centrally located core material, is done with a polymer gel. This refilling step 812 differs from that of the conventional phaco-ersatz method in that refilling is only into the void volume created by the removal of only the more centrally located lens core 129 material.

The polymer gel used in step 812 has the appropriate physical (e.g. mechanical, optical) properties to support accommodation. The polymer gel may be fixed intracapsularly by curing. Curing may involve any of the curing techniques available to polymer chemists including photocuring, thermal curing, or Part A/Part B type curing.

To minimize changes in IOP during the steps of opening the capsule flap and removing the chopped nucleus matter, the surgeon may, between steps 808 and 810 insert an anterior chamber (AC) maintainer, a cannula connected to an irrigation bottle maintained at a distance of 20 to 50 cm above the patient's eye. This can be done by pushing the AC maintainer though the corneal epithelium and Bowman's layer that remains above the auxiliary corneal incision the fs-laser has prepared. IOP will thus be maintained and adjusted by raising or lowering the infusion bottle. The surgeon next inserts a micro spatula through the epithelium and Bowman layer that is immediately above the main clear cornea incision the fs-laser has prepared. With the spatula, the surgeon lifts the partial capsular flap and turns it over on the remaining capsule edge, leaving the gullet open. The surgeon then completes step 810, for example by inserting a miniature aspiration cannula and removing the fragmented nucleus while leaving the surrounding cortex intact. In step 812 he/she then refills the void space with the preselected polymer (preloaded in a 0.5 cc syringe terminated with a thin cannula) and, using the spatula, repositions the capsular flap onto the gullet, therefore closing the capsular opening. An alternative is to insert a capsular sealing valve.

An autorefractor 908 may be used during refilling of the lens with polymer gel to provide guidance as to when the lens is correctly re-filled. Because only a portion of the lens core has been removed, the curvature of the void to be refilled will often be greater (i.e. have a lesser radius of curvature) than the curvature of the lens capsule. This results in a more rapid change in lens shape during lens refilling. The autorefractor 908 may be used intermittently to measure the refractive state of the eye, so that the surgeon partially refills the lens, measures the refractive state, adds more gel to the lens and then measures the refractive state again, continuing until a required refractive state is reached. However, if the autorefractor 908 forms part of or an addition to the surgical microscope, real-time refractive measurements may be taken. A refractor suitable for providing real-time measurements is described in U.S. patent application No. 61/453,090, the entire content of which is hereby incorporated herein by reference.

The specific 3D shape of the ablations made in step 802 (defining the shape of the inner core to be removed) may be varied. In some embodiments, generally shown in the accompanying Figures, the boundary of the inner core to be removed generally follows the shape of the lens, but has a wider distance between the lens capsule and the removed inner core at the equatorial region.

The remaining natural lens core and the gel provided in the evacuated lens core may have different refractive indexes. This provides an additional variable for influencing the refractive properties of the lens with the gel. The location and curvature of the anterior 303 and/or posterior 304 bounding cuts made in step 808, the refractive index of the polymer gel used in step 812 as well as the resultant thickness of the polymer gel lying in the refilled lens, may be selected so that in combination, they achieve a desired supplementary refractive power. This supplementary refractive power may be used to enhance vision e.g. by the correction of the initial refractive error of the eye.

Figure 8:
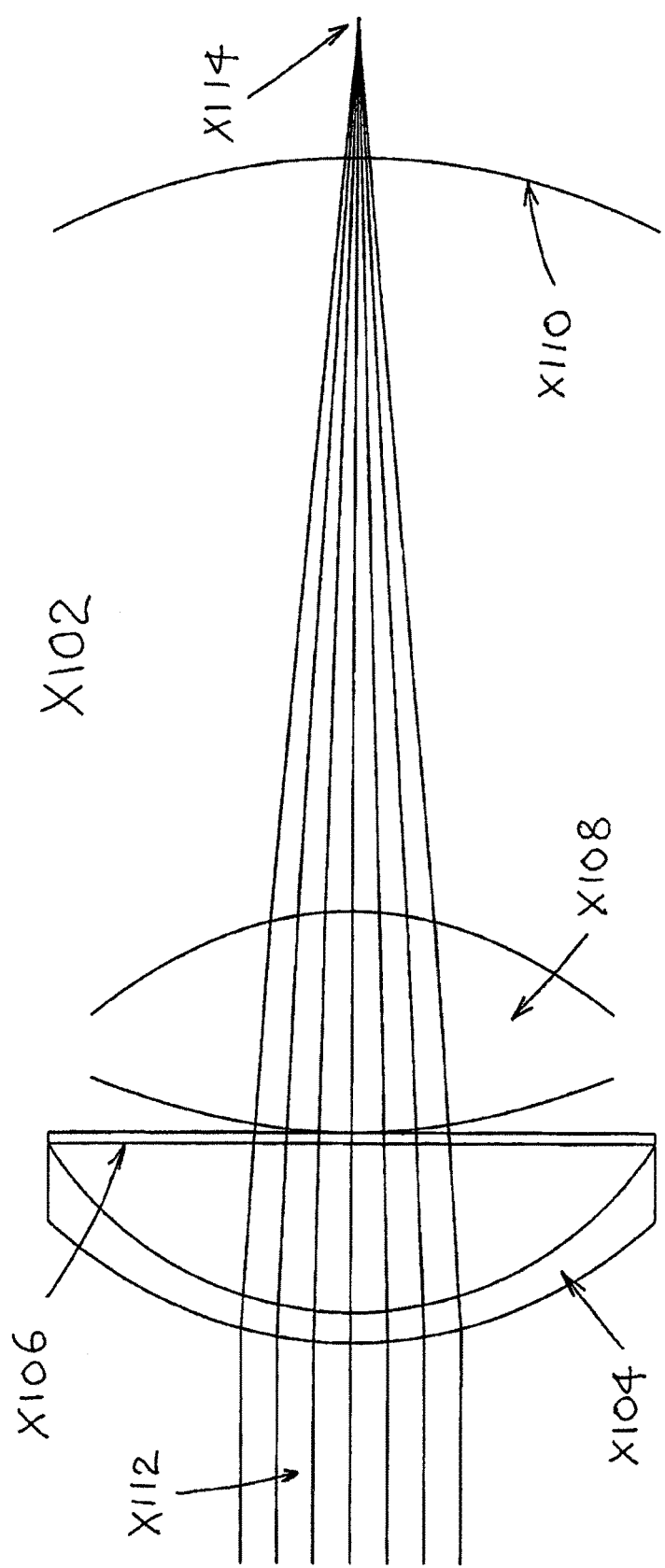
FIG. 8 shows a presbyopic eye which is also hyperopic before treatment.

The specific 3D shape of the boundary cut (defining the shape of the inner core to be removed) may also be optimised (especially at the equatorial region) for facilitating the optional introduction/implantation of a supplementary endocapsular lenticule (SECL). For example, a circular 'suture' can be cut into the lens core at the equator for positioning the edge of the lenticule to hold it in place prior to lens refilling. The endocapsular lenticule may be placed against, attached to or inserted into a portion of the lens core. The endocapsular lenticule can be attached to the cortex by welding it using the same fs-laser used to form the ablations laser. A suitable technique is described, in U.S. Pat. No. 7,060,095, the entire content of which is hereby incorporated herein by reference, whereby the SECL is embedded in the gel: the lenticule is placed first, and the gel is injected afterwards. In other embodiments, a dove-tail section is formed in the remaining lens core to capture or slot the edge/haptic of the SECL in place. Referring to FIG. 8, this optional step of including a SECL is implemented after removing the central nucleus material 810 and before refilling the central nucleus 812 when using the method as described in U.S. Pat. No. 7,060,095. It will be understood that it may also be possible to insert the SECL during or after the refilling step 812.

The endocapsular lenticule may have a refractive power itself and/or may reshape the cornea to provide a desired change in refractive power. A supplementary endocapsular lenticule 600 is shown in FIG. 6. The endocapsular lenticule 600 lies within the refilled polymer gel 503 and the edge of the SECL may extend beyond the refilled region. Typically, it should lie in the plane of least flexure (otherwise accommodation is working against its rigidity).

The plane of least flexure is typically an area or surface within the refilled lens which, during the act of accommodation (i.e. a change in lens shape) the surface flexes the least relative to any other definable transverse surface/plane within the lens. In the natural lens and in a conventional post-phaco-ersatz lens, this plane is near the posterior surface of the lens as shown in FIG. 6. However, in a lens refilled according to partial core removal as described herein, the position and extent of this plane may be different, determinable based on the size and shape of the lens as well as the mechanical properties of the remaining cortex and the refilling polymer gel.

From the description provided above, it will be appreciated that all four of the listed challenges may be improved upon.

One of the stimuli for unregulated proliferation of LEC (thereby producing disorganised, optically opaque layers of LEC—commonly known as PCO) following extraction of lens core material is the loss of contact between the capsule and LEC with the lens cortex (the LEC acts to eliminate any void volume between the capsule and lens core material). With the removal of only the more centrally located lens core material and avoiding the removal of lens core material immediately adjacent to the capsule (LEC layers), the method described herein eliminates the existence of a void volume between the capsule and the lens core (i.e. the natural lens cortex abutting or in close proximity to the capsule remains undisturbed, thereby maintaining close contact between capsule and cortex). Consequently one of the primary stimuli for LEC proliferation and PCO is removed.

Because only the more centrally located lens core material is removed and removal of lens core material immediately adjacent to the capsule is avoided, the benefit of eliminating stimulus for unregulated proliferation of LEC causing PCO is achieved. Consequently, the surgeon no longer needs to ensure removal of LEC to prevent PCO. Both the obviation of removal of LEC as well as the need to only remove the more centrally located lens core material brings the benefit that the aspirator or phaco-probe used for lens extraction does not need to be brought near the lens capsule. This significantly reduces the risk of capsule rupture or tearing due to inadvertent application of direct suction on the internal capsular surface.

By obviating the need to remove the lens core material towards the equator of the lens, and removing and refilling only the more central lens core material, the void volume at the equatorial region of the lens that typically exists following the conventional phaco-ersatz technique is eliminated. Thus, continuous mechanical coupling from ciliary body via zonules to capsule and on to the cortex and the refilling gel is maintained. This improves the efficacy of accommodation over that achievable by the conventional phaco-ersatz technique.

As only the more central lens core material is removed and refilled, the entirety of lens refilling gel may remain immediately below the dilated pupillary region. That is, the little refilling gel that does lie immediately behind and in the shadow cast by the iris can still be reached by the curing light source. For photo-curing refilling gel, this ensures completeness of curing throughout the entire refilled gel volume. One obvious benefit is the significant reduction of potential leakage of uncured gel into the anterior chamber (and beyond) posing risks of adverse physiological responses.

The present method can also be used to enhance the visual optical outcome, in particular by the partial or total correction of a pre-existing refractive error in the eye. By the selection of the appropriate curvatures or profiles of the anterior and posterior bounding cuts; the refractive index of the polymer gel (which may be higher or lower than the lens cortex material); and the thickness of the polymer gel in the refilled lens, supplementary refractive power or optical aberrations may be introduced to the optical outcome of this procedure.

The shape of the void volume for injection may be manipulated independently of the shape of the refilled crystalline lens. Thus, additional degrees of freedom in design parameters, including anterior and posterior bounding surface profiles, and thickness of refilled void volume, as well as refractive index of the polymer gel, may be varied for controlling performance characteristics in addition to refractive error, for example the optical aberration of the whole eye.

Example 1: Simultaneous Correction of Refractive Error

FIG. 8 is an optical layout modelled using an optical ray-tracing program showing a presbyopic eye X102 which can benefit from restoration of accommodation, thereby regaining continuous-focus near vision. FIG. 8 also details the cornea X104, iris/pupil X106, crystalline lens X108 and retina X110 of eye X102. It is seen that this eye suffers from hyperopia as incoming light rays X112 are focused by this eye to focus X114 such that the focus X114 lies behind the retina X110. The amount of hyperopia exhibited by eye X102 is +8 D.

Figure 9:
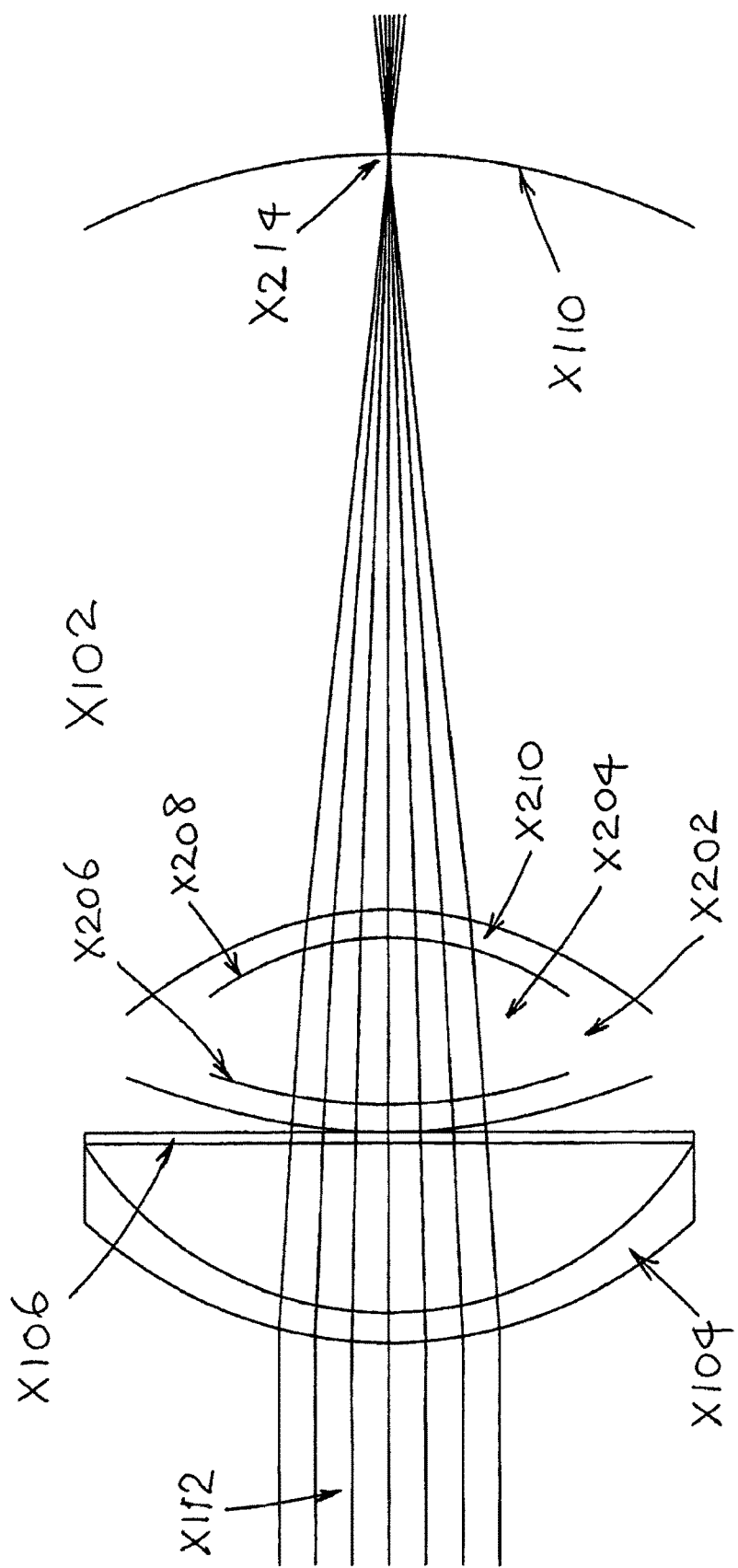
FIG. 9 shows the same eye of FIG. 8 following treatment including simultaneous correction of hyperopia.

FIG. 9 is an optical layout modeled using an optical ray-tracing program showing the same eye X102 of FIG. 8 following treatment using the method of the present invention. Thus the crystalline lens X202 has now been refilled by injecting a polymer gel into the void volume X204. The anterior X206 and posterior X208 bounding surfaces of the polymer gel in the refilled void volume X204 is placed such that the remaining outer cortex X210 is a uniform 0.5 mm thick. This renders a radius of curvature of 9.70 mm (i.e. 0.5 mm less than the lens's 10.2 mm anterior radius of curvature) for the anterior bounding surface X206. Similarly, the radius of curvature of the posterior bounding surface X208 is −5.50 mm (the negative value indicating a curvature which is concave towards the front of the eye). In this example, the refractive index of the polymer gel in the void volume X204 has been selected to be 1.465, higher than the natural lens refractive index of 1.420. Using this refractive index polymer gel, it can be seen from FIG. 9 that the initial +8 D hyperopia has been neutralized; incoming light rays X112 now creating the focus X214 on the retina X110.

Figure 10:
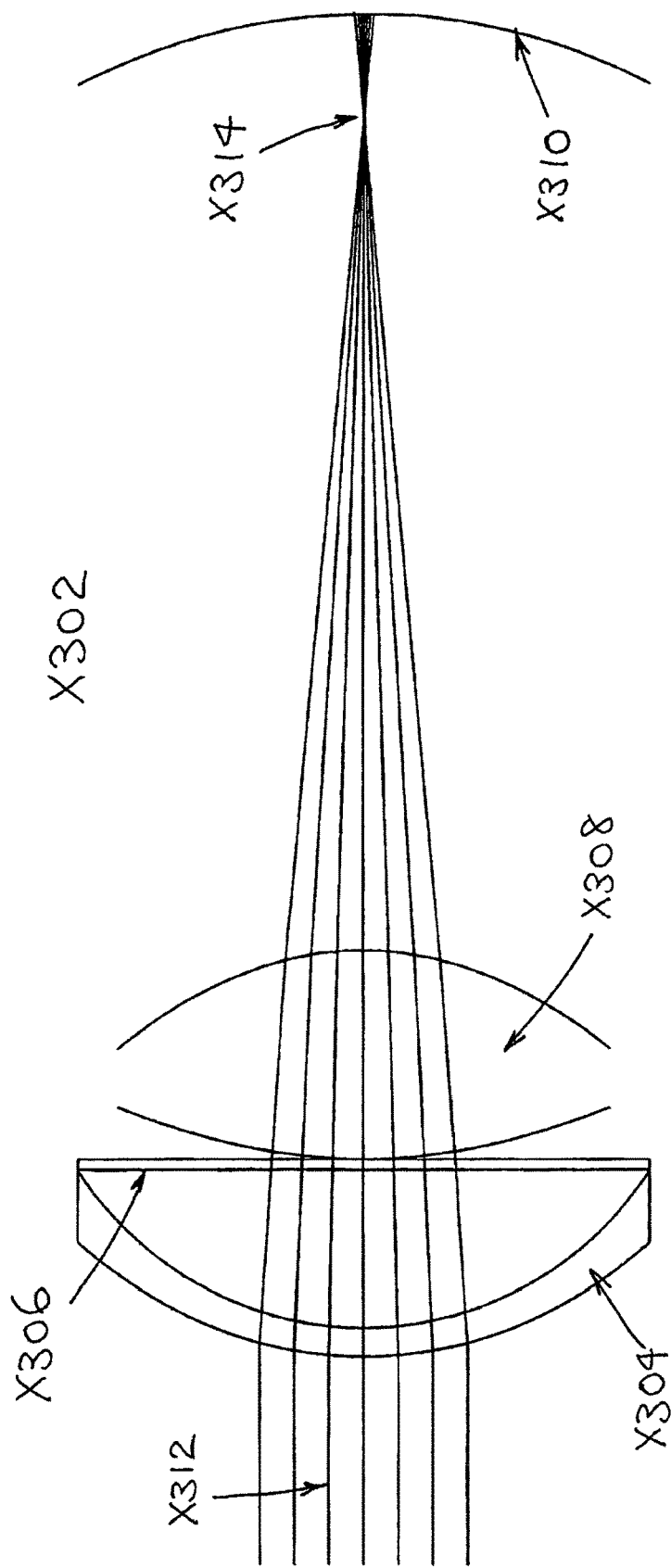
FIG. 10 shows a presbyopic eye which is also myopic and also suffers from spherical aberration before treatment.

Example 2: Simultaneous Correction of Refractive Error and Control of Spherical Aberration FIG. 10 is an optical layout modelled using an optical ray-tracing program showing a presbyopic eye X302 which can benefit from restoration of accommodation. FIG. 10 also details the cornea X304, iris/pupil X306, crystalline lens X308 and retina X310 of eye X302. It is seen that this eye suffers from myopia as incoming light rays X312 are focused by this eye to focus X314 in front of the retina X310. The amount of myopia exhibited by eye X302 is −5 D.

Figure 11:
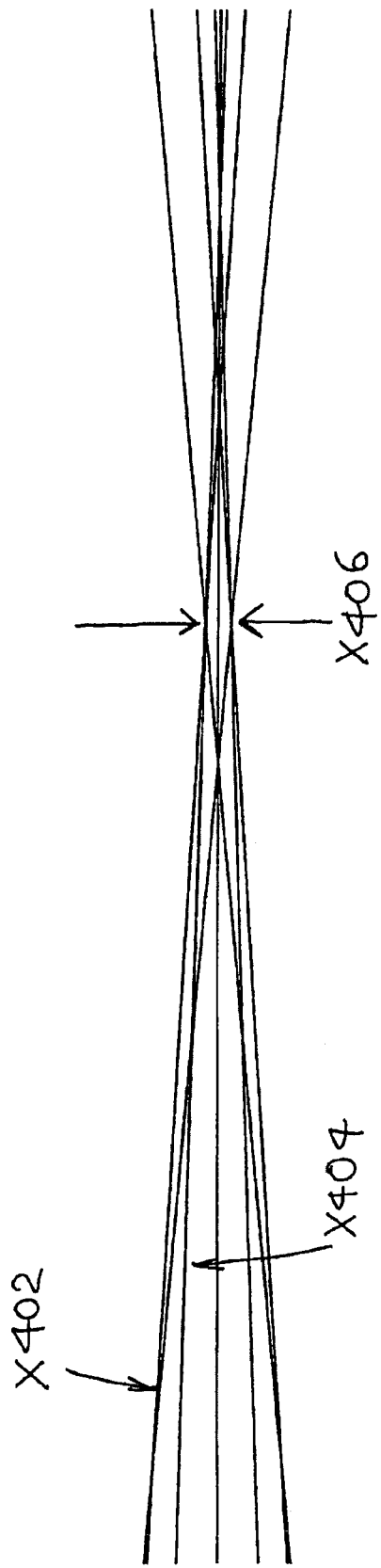
FIG. 11 shows a highly magnified view of the light rays near the focus of the eye of FIG. 10.

In addition to its myopic refractive error, this eye X302 also suffers from about 940 μm of spherical aberration (in this example, described as Seidel spherical aberration $S_1$ as understood by those skilled in the art). FIG. 11 is a highly magnified view of the light rays near the focus X314. It can be seen that the more marginal light rays X402 are focused more anteriorly (towards the left in FIG. 11) while the more central light rays X404 are focused more posteriorly. This is typical of positive spherical aberration and results in the focus X314 not being a sharp point but a blurred circle X406 even if the refractive error is corrected.

Figure 12:
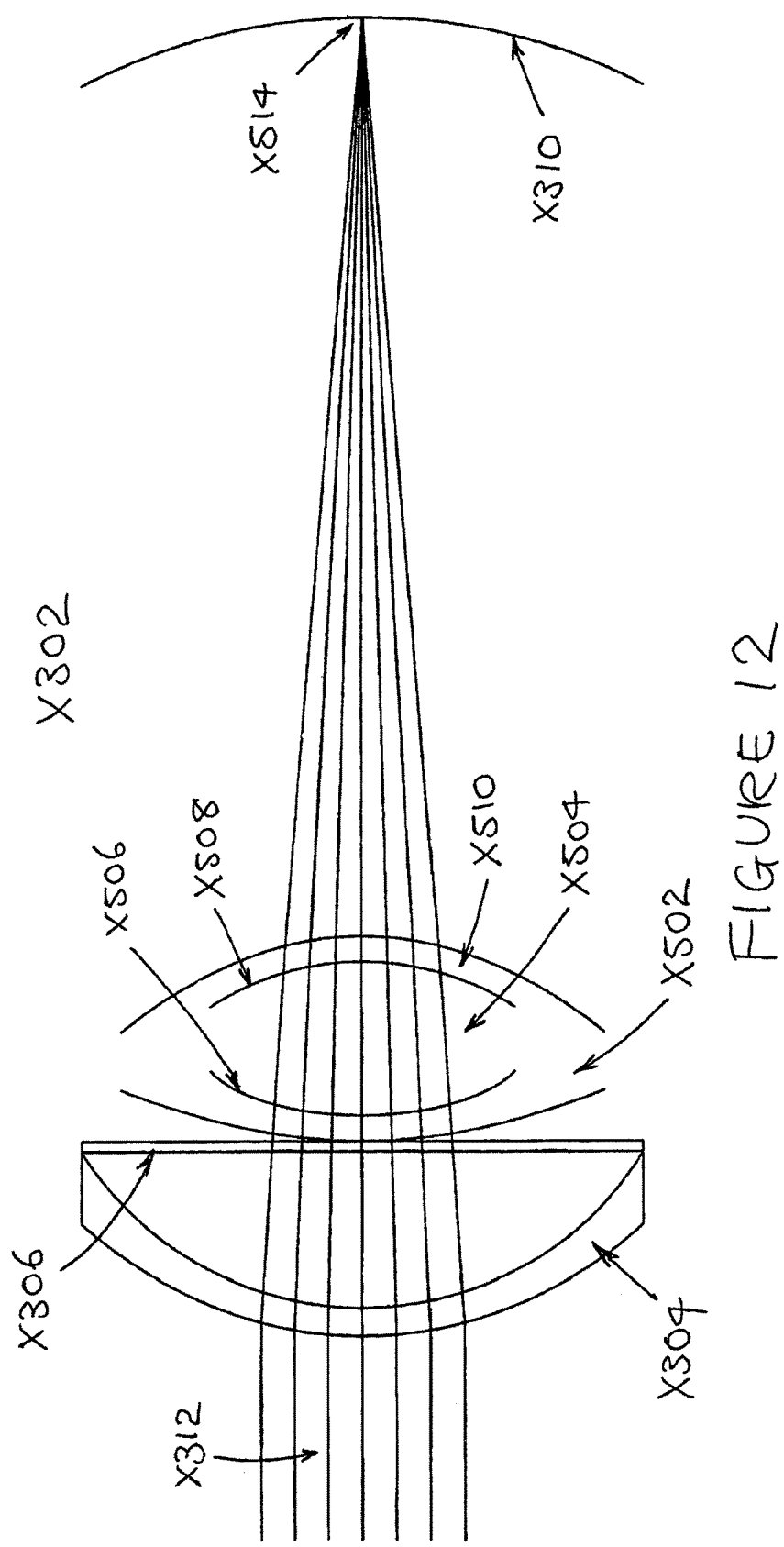
FIG. 12 shows the same eye of FIG. 10 following treatment including simultaneous correction of myopia as well as neutralization of spherical aberration.

FIG. 12 is an optical layout modelled using an optical ray-tracing program showing the same eye X302 of FIG. 10 following treatment using the method of the present invention. The crystalline lens X502 has now been refilled by injecting a polymer gel into the void volume X504. The anterior X506 and posterior X508 bounding surfaces of the polymer gel in the refilled void volume X504 is placed such that the remaining outer cortex X510 is 0.5 mm thick both anteriorly and posteriorly at the centre of the lens X502.

In this example, an aspheric profile was selected for the anterior bounding surface X506. This aspheric profile is described by a conic section in which its central radius is 7.447 mm with a conic constant (k) of 3.262. Similarly, an aspheric profile was also selected for the posterior bounding surface X508 whose central radius is −5.500 mm and conic constant is 6.940. With this choice of surface profiles for the two bounding surfaces X506, X508, using a polymer gel with refractive index 1.400 (i.e. lower than that of the natural lens) corrects the myopia of eye X302 by placing the focus X514 on the retina X310 and also neutralizes its spherical aberration; residual spherical aberration being much less than 1 μm.

The neutralization of spherical aberration is illustrated in FIG. 13 which is a highly magnified view of the light rays X612 near the focus X514. It can be seen that all light rays X612 after refraction through the eye X302 are now directed precisely to focus X514 creating a sharp focal point on the retina X310.

It will be clear that other combinations of values for parameters including anterior and posterior bounding surface profiles, void volume thickness, anterior and posterior remaining outer cortex thicknesses and refractive index of gel, can be used to achieve other improvements in the visual outcome of a post-treatment eye. It will also be clear that in addition to conic sections, other aspheric profiles (including polynomials, splines, Fourier syntheses, etc) may also be used to manipulate the profiles of the anterior and posterior bounding surfaces.

The dimensions of the removed central portion and hence the dimensions of the replacement synthetic material (e.g. polymer gel) may be selected so that substantially all on-axis light entering the eye through the pupil when the pupil is dilated traverses through said synthetic material. These dimensions may be selected whether or not the polymer gel is designed to effect a particular optical outcome, as it may avoid undesirable effects at the peripheral edges of the synthetic material.

Where the visual optical outcome is to be modified by the optical properties of the synthetic replacement lens material, then the replacement lens material may be allowed to contact the lens capsule in some locations. The replacement lens material may contact the lens capsule at the equatorial regions, at the anterior hemisphere and/or at the posterior hemisphere. While this may result in one or more of the disadvantages described herein associated with contact of the replacement lens material, it is foreseeable that in at least some instances these disadvantages, or the potential for the disadvantages, are acceptable.

Thus the method described herein will maximise the potential of accommodative gel used in a lens refilling procedure by eliminating a stimulus for PCO, significantly reducing the risk of capsule rupture, improving mechanical accommodative efficacy and ensuring completeness of curing thereby significantly reducing risk of adverse response. Therefore, this method improves the functional working life of the technology for the patient; improves near vision; reduces the chance that a patient may be relegated from being eligible for lens refilling; and improves compatibility.

It will be understood that the invention disclosed and defined in this specification extends to all alternative combinations of two or more of the individual features mentioned or evident from the text or drawings. All of these different combinations constitute various alternative aspects of the invention.

What is claimed is:

1. A method for refilling a lens of an eye having a lens with a lens core comprising a cortex surrounding a central nucleus, a lens capsule and lens epithelial cells enclosing the lens core and a cornea, the method comprising:
   a) removing a central portion of the lens core through the cornea to create a void volume in the lens by creating in a postero-anterior order:
      i) first, a posterior bounding ablation;
      ii) second, a series of chopping ablations in a postero-anterior order and in a peripheral to central order, wherein:
         1) moving from posterior layers to anterior layers of the central portion of the lens core, posterior portions of the series of chopping ablations are created prior to anterior portions of the series of chopping ablations; and
         2) for a respective layer of said central portion of the lens core, all peripheral portions of the series of chopping ablations are created prior to central portions of the series of chopping ablations; and
      iii) third, an anterior bounding ablation;
   b) creating an opening in the lens capsule;
   c) creating a gullet extending through the cortex from the opening to the void volume; and
   d) filling the void volume through the opening and gullet with a synthetic lens material.

2. The method of claim 1, wherein removing a central portion of the lens core comprises removing the central nucleus and not any of the cortex.

3. The method of claim 1, wherein removing a central portion of the lens core comprises removing the central nucleus and a central portion of the cortex.

4. The method of claim 3, wherein removing a central portion of the lens core comprises leaving at least between 10 μm and 50 μm of cortex in place adjacent the anterior lens capsule.

5. The method of claim 4, wherein removing a central portion of the lens core comprises leaving at least between 10 μm and 50 μm of cortex in place adjacent the posterior lens capsule.

6. The method of claim 3, wherein removing a central portion of the lens core comprises leaving at least 25 μm of cortex in place adjacent the anterior lens capsule.

7. The method of claim 3, wherein removing a central portion of the lens core comprises leaving at least 50 μm of cortex in place adjacent the anterior lens capsule.

8. The method of claim 3, wherein removing a central portion of the lens core comprises leaving at least 75 μm of cortex in place adjacent the anterior lens capsule.

9. The method of claim 1 wherein removing a central portion of the lens core removes at least 12.5% of the volume of the lens core.

10. The method of claim 1 wherein removing a central portion of the lens core removes at least 30% of the volume of the lens core.

11. The method of claim 1, wherein the filling the void volume with a synthetic material comprises selecting a synthetic material with a refractive index that, in combination with a shape expected to be formed by the synthetic material when filling the void volume, provides a correction of refractive error in the eye.

12. The method of claim 1, further comprising creating an opening in the lens capsule, wherein the void volume is filled through the opening and the gullet.

13. A method for increasing elasticity of the lens of an eye, the method comprising:
   a) removing a central portion of a lens core of the eye thereby creating a void volume by creating in a postero-anterior order:
      i) first, a posterior bounding ablation;
      ii) second, a series of chopping ablations in a postero-anterior order and in a peripheral to central order, wherein:
         1) moving from posterior layers to anterior layers of the central portion of the lens core, posterior portions of the series of chopping ablations are created prior to anterior portions of the series of chopping ablations; and
         2) for a respective layer of said central portion of the lens core, all peripheral portions of the series of chopping ablations are created prior to central portions of the series of chopping ablations; and
   b) filling the void volume with a synthetic material of higher elasticity than the removed central portion of the lens core, wherein removing the central portion of the lens core comprises leaving sufficient lens core in place so that the synthetic material is not in contact with a lens capsule of the eye.

14. The method of claim 13, comprising leaving sufficient lens core in place so that lens epithelial cells along an anterior hemisphere of the lens capsule remain intact.

15. The method of claim 13, wherein leaving sufficient lens core in place so that the synthetic material is not in contact with a lens capsule of the eye comprises leaving a greater thickness of lens core material in place in an equatorial region of the lens than in the anterior hemisphere of the lens.

16. The method of claim 13, wherein leaving sufficient lens core in place so that the synthetic material is not in contact with a lens capsule of the eye comprises leaving a greater thickness of lens core material in place in an equatorial region of the lens than in the anterior and posterior hemispheres of the lens.

17. The method of claim 13, further comprising inserting an endocapsular lenticule against, attached to or into the lens so that the endocapsular lenticule affects refractive characteristics of the lens.

18. A method of altering the elasticity of an eye comprising a pupil, a lens and a retina, the method comprising:
a) removing a portion of a core of the lens by creating in a postero-anterior order:
  i) first, a posterior bounding ablation:
  ii) second, a series of chopping ablations in a postero-anterior order and in a peripheral to central order, wherein:
    1) moving from posterior layers to anterior layers of the central portion of the lens core, posterior portions of the series of chopping ablations are created prior to anterior portions of the series of chopping ablations; and
    2) for a respective layer of said central portion of the lens core, all peripheral portions of the series of chopping ablations are created prior to central portions of the series of chopping ablations; and
  iii) third, an anterior bounding ablation; and
b) filling a resultant void volume in the lens with a synthetic material of higher elasticity than the removed portion;
wherein the removing a portion of a core of the lens is controlled so that after the filling, light entering the eye through a pupil of the eye, before being received by the retina, traverses through a portion of lens core that was not removed and through the synthetic material.

19. The method of claim 18, wherein said controlled removing is effected so that after the filling, light entering the eye through a pupil of the eye, before being received by the retina, traverses through an anterior portion of lens core that was not removed, through the synthetic material and then through a posterior portion of the lens core that was not removed.

20. The method of claim 18, wherein said controlled removing is effected so that all on-axis light entering the eye through the pupil when the pupil is dilated traverses through said synthetic material.

21. A method of altering the elasticity and the refractive characteristics of an eye comprising a pupil, a lens and a retina, the method comprising:
a) removing a portion of a core of the lens to create a void volume and leaving a remaining lens core by creating in a postero-anterior order:
  i) first, a posterior bounding ablation;
  ii) second, a series of chopping ablations in a postero-anterior order and in a peripheral to central order, wherein:
    1) moving from posterior layers to anterior layers of the central portion of the lens core, posterior portions of the series of chopping ablations are created prior to anterior portions of the series of chopping ablations; and
    2) for a respective layer of said central portion of the lens core, all peripheral portions of the series of chopping ablations are created prior to central portions of the series of chopping ablations; and
  iii) third, an anterior bounding ablation; and
b) filling the void volume with a synthetic material of higher elasticity than the removed portion of the lens core and of a different refractive index to the remaining lens core;
wherein the removing a portion of a core of the lens is controlled so that after the void volume has been filled with the synthetic material, light entering the eye through a pupil of the eye, before being received by a retina of the eye, traverses through a portion of the remaining lens core and through the synthetic material and is refracted so as to at least partially correct refractive error in the eye.

22. The method of claim 21, wherein the removing a portion of a core of the lens is controlled so that the synthetic material forms a shape to provide a power for said light entering the eye, the power selected to provide the at least partial correction of refractive error in the eye.

23. A method of altering the elasticity and refractive characteristics of a lens of an eye comprising a pupil and a retina, the method comprising:
a) removing a portion of a core of the lens to create a void volume in the lens and leaving a remaining lens core by creating in a postero-anterior order:
  i) first, a posterior bounding ablation;
  ii) second, a series of chopping ablations in a postero-anterior order and in a peripheral to central order, wherein:
    1) moving from posterior layers to anterior layers of the central portion of the lens core, posterior portions of the series of chopping ablations are created prior to anterior portions of the series of chopping ablations; and
    2) for a respective layer of said central portion of the lens core, all peripheral portions of the series of chopping ablations are created prior to central portions of the series of chopping ablations; and
  iii) third, an anterior bounding ablation
b) filling the void volume with a synthetic material of higher elasticity than the removed material; and
c) inserting an endocapsular lenticule against, attached to or into the lens so that the endocapsular lenticule affects refractive characteristics of the lens.

* * * * *